US012605109B2

(12) United States Patent
Yang et al.

(10) Patent No.: US 12,605,109 B2
(45) Date of Patent: Apr. 21, 2026

(54) APPARATUS AND METHOD FOR DETERMINING BRAIN LANGUAGE AREA INVASION BASED ON SPEECH DATA

(71) Applicants: THE CATHOLIC UNIVERSITY OF KOREA INDUSTRY-ACADEMIC COOPERATION FOUNDATION, Seoul (KR); UNIVERSITY OF SEOUL INDUSTRY COOPERATION FOUNDATION, Seoul (KR)

(72) Inventors: Seung Ho Yang, Seoul (KR); Young Il Kim, Suwon-si (KR); Ha Jin Yu, Seoul (KR)

(73) Assignees: THE CATHOLIC UNIVERSITY OF KOREA INDUSTRY-ACADEMIC COOPERATION FOUNDATION, Seoul (KR); UNIVERSITY OF SEOUL INDUSTRY COOPERATION FOUNDATION, Seoul (KR)

( * ) Notice: Subject to any disclaimer, the term of this patent is extended or adjusted under 35 U.S.C. 154(b) by 220 days.

(21) Appl. No.: 18/406,418

(22) Filed: Jan. 8, 2024

(65) Prior Publication Data

US 2024/0252106 A1 Aug. 1, 2024

(30) Foreign Application Priority Data

Jan. 30, 2023 (KR) ........................ 10-2023-0011444

(51) Int. Cl.
*G10L 15/18* (2013.01)
*A61B 5/00* (2006.01)
(Continued)

(52) U.S. Cl.
CPC .......... *A61B 5/4803* (2013.01); *A61B 5/0042* (2013.01); *A61B 5/055* (2013.01);
(Continued)

(58) Field of Classification Search
CPC ..... A61B 5/4803; A61B 5/0042; A61B 5/055; A61B 5/4064; A61B 5/7267;
(Continued)

(56) References Cited

U.S. PATENT DOCUMENTS

| | | | |
|---|---|---|---|
| 12,296,265 B1 * | 5/2025 | Gupta | .................... G10L 19/04 |
| 2015/0297106 A1 * | 10/2015 | Pasley | ................... A61B 5/741 |
| | | | 600/383 |

(Continued)

FOREIGN PATENT DOCUMENTS

| | | |
|---|---|---|
| JP | 2020-000483 A | 1/2020 |
| KR | 10-2001398 B1 | 7/2019 |
| KR | 10-2216160 B1 | 2/2021 |

OTHER PUBLICATIONS

An Office Action mailed by the Korean Intellectual Property Office on Sep. 3, 2024, which corresponds to Korean Patent Application No. 10-2023-0011444 and is related to U.S. Appl. No. 18/406,418.

*Primary Examiner* — Fariba Sirjani

(74) *Attorney, Agent, or Firm* — Studebaker Brackett PLLC

(57) ABSTRACT

Disclosed is a language area invasion determination apparatus including a memory unit including a language area invasion determination model, and a processor that controls an operation of the language area invasion determination model included in the memory unit. The processor trains the language area invasion determination model by using one or more training utterance data and outputs language area invasion determination data of an examiner by using test (Continued)

utterance data and the trained language area invasion determination model. The training utterance data and the test utterance data include utterance speech data of a speaker.

20 Claims, 6 Drawing Sheets

(51) Int. Cl.
| | | |
|---|---|---|
| *A61B 5/055* | (2006.01) | |
| *G10L 13/02* | (2013.01) | |
| *G10L 15/06* | (2013.01) | |
| *G10L 25/66* | (2013.01) | |

(52) U.S. Cl.
CPC .......... *A61B 5/4064* (2013.01); *A61B 5/7267* (2013.01); *G10L 15/063* (2013.01); *G10L 15/18* (2013.01); *G10L 25/66* (2013.01); *A61B 2576/026* (2013.01); *G10L 13/02* (2013.01)

(58) Field of Classification Search
CPC ............ A61B 2576/026; A61B 5/7275; G10L 15/063; G10L 15/18; G10L 25/66; G10L 13/02; G06N 3/04; G06N 3/08; G16H 50/20
See application file for complete search history.

(56) References Cited

U.S. PATENT DOCUMENTS

| | | | | |
|---|---|---|---|---|
| 2019/0180878 A1* | 6/2019 | Fridriksson | ............ | G16H 20/40 |
| 2022/0068261 A1* | 3/2022 | Sharifi | ..................... | G06F 3/16 |
| 2022/0301563 A1* | 9/2022 | Chang | .................... | G10L 15/24 |
| 2022/0358657 A1* | 11/2022 | Murray | ................. | G06T 7/0014 |
| 2022/0378361 A1* | 12/2022 | Lee | ...................... | A61B 5/7275 |
| 2023/0123659 A1* | 4/2023 | Slutzky | ................ | A61B 5/7267 |
| | | | | 600/544 |
| 2023/0154485 A1* | 5/2023 | Jeong | ..................... | G10L 25/30 |
| | | | | 381/56 |
| 2023/0162719 A1* | 5/2023 | Ayyad | .................... | G06N 3/096 |
| | | | | 704/260 |
| 2023/0178094 A1* | 6/2023 | Amid | ....................... | H04K 3/90 |
| | | | | 704/200 |
| 2023/0410789 A1* | 12/2023 | Sharma | ................. | G10L 13/033 |
| 2024/0144478 A1* | 5/2024 | Choi | ........................ | A61B 3/10 |
| 2024/0252106 A1* | 8/2024 | Yang | ..................... | G10L 25/66 |
| 2025/0068841 A1* | 2/2025 | Huth | ..................... | A61B 5/741 |

* cited by examiner

| Utterance data | Speech data | Transcript data | Brain image | fMRI determination result | DTI tractography determination result | Intraoperative mapping determination result |
|---|---|---|---|---|---|---|
| 1 | V1 | T1 | B1 | 44 | 44 | 44 |
| 2 | V2 | T2 | B2 | 45 | 45 | 48 |
| 3 | V3 | T3 | B3 | 49 | 42 | 47 |

APPARATUS AND METHOD FOR DETERMINING BRAIN LANGUAGE AREA INVASION BASED ON SPEECH DATA

CROSS-REFERENCE TO RELATED APPLICATIONS

A claim for priority under 35 U.S.C. § 119 is made to Korean Patent Application No. 10-2023-0011444 filed on Jan. 30, 2023 in the Korean Intellectual Property Office, the entire contents of which are hereby incorporated by reference.

BACKGROUND

Embodiments of the present disclosure described herein relate to a method of determining whether brain language areas of brain disease lesions such as brain tumors, cerebrovascular diseases, brain inflammatory diseases, and traumatic brain injury are invaded by using speech data, and more particularly, relate to a brain language area invasion determination method using machine learning-based speech data.

A method of determining the invasion of a language area of a patient with a brain disease accompanied by conventional language impairment includes a method in which a medical expert, such as a doctor, interprets basic MRI images and then directly determines whether the language area is invaded, a method of determining whether an area activated when a patient performs language-related processing overlaps an area of a lesion such as a tumor, by using functional MRI images, or a method of determining whether a white matter tract connected to a language area is invaded, through tractography.

In this method, the doctor's subjective determination is involved when determining whether a brain language area is invaded, and thus objective determination criteria need to be presented. Moreover, in determining whether the brain language area is invaded, the conventional method necessarily involves expensive medical procedures such as MRI, which is a burden on medical professionals and patients. Accordingly, there is a need in the art for a technology capable of performing screening before detailed examination in determining whether the language area is invaded in the patient with a brain disease.

SUMMARY

Embodiments of the present disclosure provide criteria for determining whether a patient's brain language area is invaded, by using speech data.

Problems to be solved by the present disclosure are not limited to the problems mentioned above, and other problems not mentioned will be clearly understood by those skilled in the art from the following description.

According to an embodiment, a language area invasion determination apparatus includes a memory unit including a language area invasion determination model, and a processor that controls an operation of the language area invasion determination model included in the memory unit. The processor trains the language area invasion determination model by using one or more training utterance data and outputs language area invasion determination data of an examiner by using test utterance data and the trained language area invasion determination model. The training utterance data and the test utterance data include utterance speech data of a speaker.

Moreover, the training utterance data further includes the language area invasion determination data. The language area invasion determination data includes at least one of language area invasion-related data or detailed invasion area data.

Furthermore, the language area invasion-related data or the detailed invasion area data includes brain image-based data of the speaker.

Also, the brain image-based data includes a brain image of the speaker or brain image read data. The brain image includes at least one of functional MRI (fMRI), DTI tractography, and intraoperative mapping.

In addition, the training utterance data includes original utterance data, modulation utterance data, and utterance data generated by using an artificial intelligence-based text-to-speech.

Besides, the language area invasion determination model is built by using one or more neural networks, and applies an ensemble technique to the one or more neural networks.

Moreover, the applying of the ensemble technique to the one or more neural networks includes inputting, by the language area invasion determination model, utterance data into the one or more neural networks and ensembling language area invasion determination data generated from each of the one or more neural networks. The one or more neural networks use a recurrent neural network, a convolutional neural network, a transformer, and a long short-term memory.

Furthermore, the utterance data further includes utterance transcript data.

Also, the language area invasion determination model further includes a sentence reading network that receives the utterance transcript data and generates language area invasion determination data.

In addition, the sentence reading network outputs detailed invasion area data.

Besides, the processor trains an utterance function evaluation model of the speaker by using the training utterance data. The utterance function evaluation model calculates a similarity between normal utterance data and the training utterance data or the test utterance data.

Moreover, the calculating of the similarity between the normal utterance data and the training utterance data or the test utterance data includes calculating a similarity between a waveform of the normal utterance data and a waveform of the training utterance data or a waveform of the test utterance data.

According to an embodiment, a computer program, when executed by one or more processors, performs following operations for determining language area invasion by using utterance data as the computer program stored in a computer-readable storage medium, the operations include training a language area invasion determination model by using one or more training utterance data, and outputting language area invasion determination data of an examiner by using test utterance data and the trained language area invasion determination model. The training utterance data and the test utterance data include utterance speech data of a speaker.

Besides, a brain language area invasion determination method for execution to implement the present disclosure may be further provided.

In addition, a computer-readable recording medium for recording a computer program for performing the method for implementing the present disclosure may be further provided.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 4 is a conceptual diagram showing training utterance data, according to some embodiments of the present disclosure;

DETAILED DESCRIPTION

Figure 1:
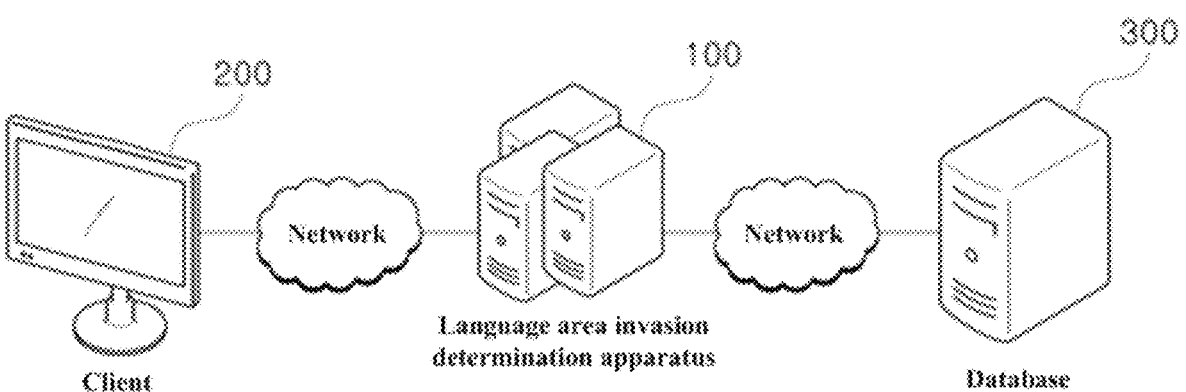
FIG. 1 is a conceptual diagram showing an overall system, according to an embodiment of the present disclosure.

The same reference numerals denote the same elements throughout the present disclosure. The present disclosure does not describe all elements of embodiments. Well-known content or redundant content in which embodiments are the same as one another will be omitted in a technical field to which the present disclosure belongs. A term such as 'unit, module, member, block, or model' used in the specification may be implemented with software or hardware. According to embodiments, a plurality of 'units, modules, members, blocks, or models' may be implemented with one component, or a single 'unit, module, member, block, or model' may include a plurality of components.

Throughout this specification, when it is supposed that a portion is "connected" to another portion, this includes not only a direct connection, but also an indirect connection. The indirect connection includes being connected through a wireless communication network.

Furthermore, when a portion "comprises" a component, it will be understood that it may further include another component, without excluding other components unless specifically stated otherwise.

Throughout this specification, when it is supposed that a member is located on another member "on", this includes not only the case where one member is in contact with another member but also the case where another member is present between two other members.

Terms such as 'first', 'second', and the like are used to distinguish one component from another component, and thus the component is not limited by the terms described above.

Unless there are obvious exceptions in the context, a singular form includes a plural form.

In each step, an identification code is used for convenience of description. The identification code does not describe the order of each step. Unless the context clearly states a specific order, each step may be performed differently from the specified order.

Hereinafter, operating principles and embodiments of the present disclosure will be described with reference to the accompanying drawings.

In this specification, an 'apparatus according to an embodiment of the present disclosure' includes all various devices capable of providing results to a user by performing arithmetic processing. For example, the apparatus according to an embodiment of the present disclosure may include all of a computer, a server device, and a portable terminal, or may be in any one form.

Here, for example, the computer may include a notebook computer, a desktop computer, a laptop computer, a tablet PC, a slate PC, and the like, which are equipped with a web browser.

The server device may be a server that processes information by communicating with an external device and may include an application server, a computing server, a database server, a file server, a game server, a mail server, a proxy server, and a web server.

For example, the portable terminal may be a wireless communication device that guarantees portability and mobility, and may include all kinds of handheld-based wireless communication devices such as a smartphone, a personal communication system (PCS), a global system for mobile communication (GSM), a personal digital cellular (PDC), a personal handyphone system (PHS), a personal digital assistant (PDA), International Mobile Telecommunication (IMT)-2000, a code division multiple access (CDMA)-2000, W-Code Division Multiple Access (W-CDMA), and Wireless Broadband Internet terminal (Wibro) terminal, and a wearable device such as a timepiece, a ring, a bracelet, an anklet, a necklace, glasses, a contact lens, or a head-mounted device (HMD).

Functions related to artificial intelligence according to an embodiment of the present disclosure are operated through a processor and a memory. The processor may consist of one or more processors. In this case, the one or more processors may be a general-purpose processor (e.g., a CPU, an AP, or a digital signal processor (DSP)), a graphics-dedicated processor (e.g., a GPU or a vision processing unit (VPU)), or an artificial intelligence-dedicated processor (e.g., an NPU). Under control of the one or more processors, input data may be processed depending on an artificial intelligence model, or a predefined operating rule stored in the memory. Alternatively, when the one or more processors are artificial intelligence-dedicated processors, the artificial intelligence-dedicated processor may be designed with a hardware structure specialized for processing a specific artificial intelligence model.

The predefined operating rule or the artificial intelligence model is created through learning. Here, being created through learning means creating the predefined operating rule or the artificial intelligence model configured to perform desired features (or purposes) as a basic artificial intelligence model is learned by using pieces of learning data by a learning algorithm. This learning may be performed by an apparatus itself that performs the artificial intelligence according to an embodiment of the present disclosure, or may be performed through a separate server and/or system. For example, the learning algorithm may include supervised learning, unsupervised learning, semi-supervised learning, or reinforcement learning, but may not be limited to the above example.

An artificial intelligence model may be composed of a plurality of neural network layers. The plurality of neural network layers respectively have a plurality of weight values, and each of the plurality of neural network layers performs neural network calculation through calculations between the calculation result of the previous layer and the plurality of weight values. The plurality of weight values of the plurality neural network layers may be optimized by the learning result of the artificial intelligence model. For example, during a learning process, the plurality of weight values may be updated such that a loss value or cost value obtained from the artificial intelligence model is reduced or minimized. The artificial neural network may include a deep neural network (DNN). The artificial neural network may be, for example, a convolutional neural network (CNN), a deep neural network (DNN), a recurrent neural network (RNN), a restricted Boltzmann machine (RBM), a deep belief network (DBN), a bidirectional recurrent deep neural network (BRDNN), or a deep Q-network, but is not limited to the above-described example.

According to an embodiment of the present disclosure, a processor may implement artificial intelligence. The artificial intelligence may refer to an artificial neural network-based machine learning method that allows a machine to perform learning by simulating human biological neurons. The methodology of artificial intelligence may be classified as supervised learning, in which a solution (output data) to a problem (input data) is determined by providing input data and output data together as training data depending on a learning method, unsupervised learning, in which only input data is provided without output data, and thus the solution (output data) to the problem (input data) is not determined, and reinforcement learning, in which a reward is given from an external environment whenever an action is taken in a current state, and thus learning progresses to maximize this reward. Moreover, the methodology of artificial intelligence may also be categorized depending on an architecture which is the structure of the learning model. The architecture of deep learning technology widely used may be categorized into convolutional neural networks (CNN), recurrent neural networks (RNN), transformers, and generative adversarial networks (GAN).

Each of the apparatus and the system may include an artificial intelligence model. The artificial intelligence model may be a single artificial intelligence model or may be implemented as a plurality of artificial intelligence models. The artificial intelligence model may be composed of neural networks (or artificial neural networks) and may include a statistical learning algorithm that mimics biological neurons in machine learning and cognitive science. The neural network may refer to a model as a whole having the ability to solve problems as artificial neurons (nodes), which form a network by connecting synapses, changes the strength of their synaptic connections through learning. Neurons in a neural network may include the combination of weight values or biases. The neural network may include one or more layers consisting of one or more neurons or nodes. For example, the apparatus may include an input layer, a hidden layer, and an output layer. The neural network constituting the apparatus may infer the result (output) to be predicted from an arbitrary input by changing a weight value of a neuron through learning.

The processor may create a neural network, may train or learn a neural network, or may perform operations based on received input data, and then may generate an information signal or may retrain the neural network based on the performed results. Models of a neural network may include various types of models such as a convolution neural network (CNN) (e.g., GoogleNet, AlexNet, or VGG Network), a region with convolution neural network (R-CNN), a region proposal network (RPN), a recurrent neural network (RNN), a stacking-based deep neural network (S-DNN), a state-space dynamic neural network (S-SDNN), a deconvolution network, a deep belief network (DBN), a restricted Boltzmann machine (RBM), a fully convolutional network, a long short-term memory (LSTM) Network, and a classification network, but is not limited thereto. The processor may include one or more processors for performing operations according to neural network models. For example, the neural network may include a deep neural network.

It will be understood by those skilled in the art that a neural network may include any neural network, but is not limited to a convolutional neural network (CNN), a recurrent neural network (RNN), a perceptron, a multilayer perceptron, a feed forward (FF), a radial basis network (RBF), a deep feed forward (DFF), a long short term memory (LSTM), a gated recurrent unit (GRU), an auto encoder (AE), a variational auto encoder (VAE), a denoising auto encoder (DAE), a sparse auto encoder (SAE), a Markov chain (MC), a Hopfield network (HN), a Boltzmann machine (BM), a restricted Boltzmann machine (RBM), a deep belief network (DBN), a deep convolutional network (DCN), a deconvolutional network (DN), a deep convolutional inverse graphics network (DCIGN), a generative adversarial network (GAN), a liquid state machine (LSM), an extreme learning machine (ELM), an echo state network (ESN), a deep residual network (DRN), a differentiable neural computer (DNC), a neural turning machine (NTM), a capsule network (CN), a Kohonen network (KN), and an attention network (AN).

According to an embodiment of the present disclosure, the processor may use various artificial intelligence structures and algorithms such as a convolution neural network (CNN) (e.g., GoogleNet, AlexNet, or VGG Network), a region with convolution neural network (R-CNN), a region proposal network (RPN), a recurrent neural network (RNN), a stacking-based deep neural network (S-DNN), a state-space dynamic neural network (S-SDNN), a deconvolution network, a deep belief network (DBN), a restricted Boltzmann machine (RBM), a fully convolutional network, a long short-term memory (LSTM) Network, a classification network, Generative Modeling, eXplainable AI, Continual AI, Representation Learning, AI for Material Design, algorithms for natural language processing (e.g., BERT, SP-BERT, MRC/QA, Text Analysis, Dialog System, GPT-3, and GPT-4), algorithms for vision processing (e.g., Visual Analytics, Visual Understanding, Video Synthesis, and ResNet), algorithms for data intelligence (e.g., Anomaly Detection, Prediction, Time-Series Forecasting, Optimization, Recommendation, and Data Creation), but is not limited thereto. Hereinafter, an embodiment of the present disclosure will be described in detail with reference to the accompanying drawings.

FIG. 1 is a conceptual diagram showing an overall system, according to an embodiment of the present disclosure.

Referring to FIG. 1, an overall system according to an embodiment of the present disclosure may include a language area invasion determination apparatus 100, a client 200, and a database 300. In some embodiments of the present disclosure, the language area invasion determination apparatus 100 may be a device that receives utterance data at the request of the client 200 and outputs a determination result regarding whether a patient's brain language area related to the utterance data is invaded. In some embodiments of the present disclosure, the utterance data may be data including utterance speech data and utterance transcript data for a pre-specified sentence. The utterance data may be a voice obtained as a patient suffering from a brain disease or a test subject utters a sentence received from an examiner, or data obtained by transcribing the voice.

In some embodiments of the present disclosure, the utterance data may have various forms depending on the status of the test subject and the purpose of the test. In a specific embodiment, the utterance data may be data generated by a speaker reading a specific sentence thus presented, data obtained by speaking depending on the examiner's utterance or standard utterance, data generated in response to a question, or data generated by answering the name of a presented object or concept or explaining it. Here, the test subject performing an utterance may be not only a patient who is the subject of medical treatment, but also a standard speaker who utters the sentence provided to generate standard utterance data. This standard speaker may be a person who does not have a brain-related disease or a person who has the ability to properly utter a predetermined sentence, such as an announcer. A specific example of a configuration of utterance data will be described later in FIG. 3.

The language area invasion determination apparatus 100 according to some embodiments of the present disclosure may output language area invasion determination data. In an embodiment, the language area invasion determination data may indicate whether a test subject has a disease in a brain language area, whether the test subject's brain language area is invaded by a lesion, or an invasion area of the test subject's brain language area. In detail, the language area invasion determination data may be expressed as Boolean data indicating whether a language area is invaded, a text for expressing an invasion area, or a scalar or vector encoded to indicate the invasion area. Detailed descriptions of the above-mentioned language area invasion determination data is described later in FIG. 3.

The language area invasion determination apparatus 100 according to some embodiments of the present disclosure may be connected to the client 200 and the database 300 through a network. The language area invasion determination apparatus 100 according to an embodiment of the present disclosure may take various physical forms such as desktops, laptops, servers, and mainframes. Moreover, as shown in FIG. 1, the language area invasion determination apparatus 100 according to an embodiment of the present disclosure may be constructed in a method of configuring two or more physical devices into a cluster.

The language area invasion determination apparatus 100 according to some embodiments of the present disclosure may be located at a physical location separate from the client 200. In an embodiment, the language area invasion determination apparatus 100 may be located at an on-premise data center that is physically distant from the client 200 or in a data center of a cloud provider. Besides, it is also possible for the language area invasion determination apparatus 100 to be present at the same physical location (e.g., within the same data center) as the client 200.

The client 200 according to some embodiments of the present disclosure may be a device that is connected to the language area invasion determination apparatus 100 through a network so as to transmit a request to the language area invasion determination apparatus 100, and to receive a response corresponding thereto. In an embodiment, compared to the language area invasion determination apparatus 100 such as a desktop or laptop, the client 200 may be a device that is relatively lightweight and portable.

The database 300 according to some embodiments of the present disclosure may be storage that stores data on which the language area invasion determination apparatus 100 performs the language area invasion determination of the present disclosure. In some embodiments of the present disclosure, the database 300 may store utterance data and videos, photos, and meta data related to the utterance data. In an embodiment, the database 300 may transmit data at the request of the language area invasion determination apparatus 100 over a network. As needed, the database 300 may store data at the request of the language area invasion determination apparatus 100.

Figure 2:
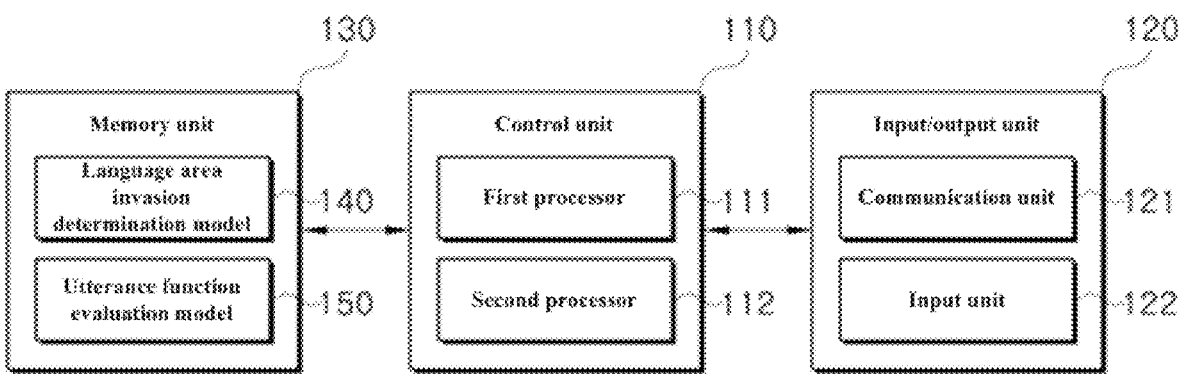
FIG. 2 is a block diagram showing a configuration of a language area invasion determination apparatus, according to an embodiment of the present disclosure.

FIG. 2 is a block diagram showing a configuration of a language area invasion determination apparatus, according to an embodiment of the present disclosure. Referring to FIG. 2, a language area invasion determination apparatus according to the present disclosure may include a control unit 110, an input/output unit 120, and a memory unit 130. The components shown in FIG. 2 are not essential in implementing a language area invasion determination apparatus according to an embodiment of the present disclosure. The language area invasion determination apparatus described herein may have more or fewer components than those listed above.

A communication unit 121 among the components may include one or more components capable of communicating with an external device, and may include, for example, at least one of a broadcast reception module, a wired communication module, a wireless communication module, a short-range communication module, and a location information module.

Here, in addition to various wired communication modules such as a Local Area Network (LAN) module, a Wide Area Network (WAN) module, or a Value Added Network (VAN) module, the wired communication module may include a variety of cable communication modules such as Universal Serial Bus (USB), High Definition Multimedia Interface (HDMI), Digital Visual Interface (DVI), recommended standard 232 (RS-232), power line communication, or plain old telephone service (POTS).

Here, the wireless communication module may include a wireless communication module for supporting various wireless communication methods such as Global System for Mobile (GSM) communication, Code Division Multiple Access (CDMA), Wideband Code Division Multiple Access (WCDMA), Universal Mobile Telecommunication System (UMTS), Time Division Multiple Access (TDMA), Long Term Evolution (LTE), 4G, 5G, and 6G in addition to a wifi module and Wireless broadband module.

An input unit may be used to enter image information (or signal), audio information (or signal), data, or information entered by a user. The input unit may include at least one of at least one camera, at least one microphone, and a user input unit. Speech data or image data collected by the input unit may be analyzed and processed as a control command of a user.

The camera may process an image frame such as a still image or a moving image, which is obtained by an image sensor in a shooting mode. The processed image frames may be stored in a memory.

In the meantime, when there are a plurality of cameras, the plurality of cameras may be arranged to form a matrix structure. In this way, pieces of image information having various angles or focuses may be input through the cameras forming a matrix structure. Furthermore, the cameras may be arranged in a stereo structure to obtain left and right images for implementing a three-dimensional stereoscopic image.

The microphone processes external acoustic signals into electrical speech data. The processed speech data may be used in various ways depending on a function (or a running application) being performed by the apparatus. In the meantime, various noise cancellation algorithms for canceling noise generated in a process of receiving an external sound signal may be implemented in a microphone.

A user input unit may be used to receive information from a user. When information is entered through the user input unit, the control unit may control operations of the apparatus to correspond to the input information. This user input unit may include a hardware-type physical key (e.g., a button, a dome switch, a jog wheel, or a jog switch that is located on at least one of the front, back, and sides of the apparatus) and a software-type touch key. For example, the touch key may consist of a virtual key, a soft key, or a visual key displayed on a touch screen-type display unit through software processing or may consist of a touch key positioned on a portion other than the touch screen. In the meantime, the virtual key or the visual key may be displayed on the touch screen while having various shapes. For example, the virtual key or visual key may be formed of graphics, texts, icons, video, or a combination thereof.

The memory may store data for supporting various functions of the apparatus, and a program for operations of the control unit, may store pieces of input/output data (e.g., music files, still images, videos, and the like), and may store a plurality of application programs (or applications) running on the apparatus, pieces of data for operations of the present apparatus, and instructions. At least part of the application programs may be downloaded from an external server through wireless communication.

The memory may include the type of a storage medium of at least one of a flash memory type, a hard disk type, a Solid State Disk (SSD) type, a Silicon Disk Drive (SDD) type, a multimedia card micro type, a memory of a card type (e.g., SD memory, XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc. Furthermore, the memory may be separate from the apparatus, but may be a database connected by wire or wirelessly.

In some embodiments of the present disclosure, the memory unit 130 may include a language area invasion determination model 140 and an utterance function evaluation model 150. When being loaded into a first processor 111 or a second processor 112 included in the control unit 110, the language area invasion determination model 140 according to some embodiments of the present disclosure may consist of one or more executable instructions that cause the first processor 111 or the second processor 112 to generate language area invasion-related data from utterance data.

Moreover, when being loaded into a first processor 111 or a second processor 112 included in the control unit 110, the utterance function evaluation model 150 according to some embodiments of the present disclosure may consist of one or more executable instructions that cause the first processor 111 or the second processor 112 to generate utterance function evaluation data of a speaker, from utterance data. Specific details of the above-mentioned language area invasion determination model and utterance function evaluation model are described in detail later in FIGS. 3 to 6.

The control unit may be implemented with a memory that stores data regarding an algorithm for controlling operations of components within the apparatus, or a program for implementing the algorithm, and at least one processor (not shown) that performs the above-described operations by using the data stored in the memory. At this time, the memory and the processor may be implemented as separate chips. Alternatively, the memory and the processor may be implemented as a single chip.

Furthermore, the control unit may control one of the components described above or the combination of the components to implement various embodiments of the present disclosure described below with reference to FIGS. 2 to 6 on the apparatus. The first processor 111 and the second processor 112 according to some embodiments of the present disclosure may be implemented by using a central processing unit, a graphic processing unit, or a neural processing unit. Moreover, the first processor 111 and the second processor 112 according to some embodiments of the present disclosure may be composed of different types of processing devices. In a specific example, the first processor 111 may be implemented by using a central processing unit, and the second processor 112 may be implemented by using a graphics processing unit. In FIG. 2, for convenience of explanation and illustration, the control unit 110 is shown as including only the first processor 111 and the second processor 112. However, the control unit 110 may include a plurality of processors depending on needs of the language area invasion determination apparatus 100.

At least one component may be added or deleted to correspond to the performance of the components illustrated in FIG. 2. Furthermore, it will be easily understood by those skilled in the art that mutual locations of the components may be changed to correspond to the performance or structure of the system.

In the meantime, each component shown in FIG. 2 refers to software components and/or hardware components such as field programmable gate array (FPGA) and application specific integrated circuit (ASIC).

Figure 3:
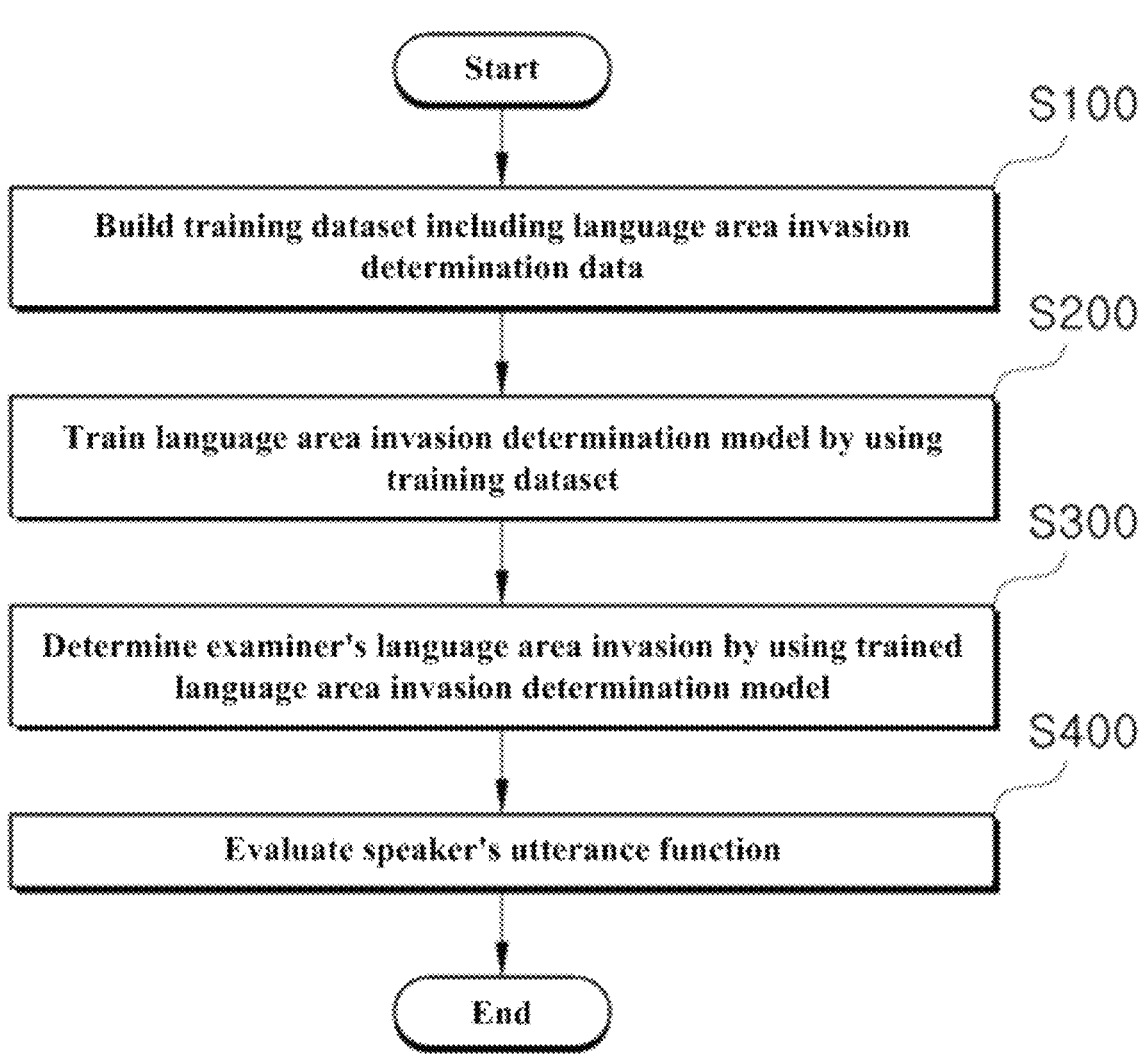
FIG. 3 is a flowchart showing a method for determining language area invasion, according to an embodiment of the present disclosure.

FIG. 3 is a flowchart showing a method for determining language area invasion, according to an embodiment of the present disclosure.

In a language area invasion determination method according to some embodiments of the present disclosure, a processor may perform a step S100 of building a training dataset including language area invasion determination data. In some embodiments of the present disclosure, the training dataset may include one or more training utterance data. In some embodiments of the present disclosure, utterance data may include training utterance data and test utterance data.

Both the training utterance data and the test utterance data may include utterance speech data. The training utterance data according to some embodiments of the present disclosure may include utterance speech data of a speaker, feature data for expressing features of the speaker, and language area invasion determination data related to whether the speaker's language area is invaded.

In some embodiments of the present disclosure, the utterance data may have various forms depending on the status of the test subject and the purpose of the test. In a specific embodiment, the utterance data may be data generated by a speaker reading a specific sentence thus presented, data obtained by speaking depending on the examiner's utterance or standard utterance, data generated in response to a question, or data generated by answering the name of a presented object or concept or explaining it.

In some embodiments of the present disclosure, the training utterance data and the test utterance data may include utterance speech data. In some embodiments, the utterance speech data may be data for expressing phonetic features of an utterance obtained as the speaker reads the presented sentence. In a specific embodiment, the utterance speech data may be a digitized time-series signal corresponding to an analog utterance, a waveform, a spectrum, a spectrogram, or an image corresponding to this digital representation. In other words, for example, the utterance speech data may include an image representation of the digitized time-series signal. Detailed descriptions of language area invasion determination data are given later with reference to FIG. 4.

The processor according to some embodiments of the present disclosure may train a language area invasion determination model by using a training dataset (S200). In some embodiments of the present disclosure, the language area invasion determination model may be implemented based on one or more neural networks. In some embodiments of the present disclosure, the training of the language area invasion determination model may mean that the language area invasion determination model in an initial state of the language area invasion determination model transforms utterance data into data in a state capable of outputting information about the speaker's brain language area invasion state at an accuracy higher than a preset level. In some embodiments of the present disclosure, training of this language area invasion determination model may mean changing weight values of one or more neural networks constituting the language area invasion determination model from the initial state. One or more loss functions may be used in the training.

The processor according to some embodiments of the present disclosure may output an examiner's language area invasion determination data by using the trained language area invasion determination model (S300). In some embodiments of the present disclosure, the processor may input the test utterance data into the trained language area invasion determination model and may output the language area invasion determination data of the examiner, who is the speaker of the test utterance data.

In some embodiments of the present disclosure, the language area invasion determination data output by the trained language area invasion determination model may include various pieces of information about whether the examiner's language area is invaded. In particular, the language area invasion determination data may include language area invasion-related data and detailed invasion area data. In a specific embodiment, the language area invasion-related data may indicate information about whether a brain language area, which encompasses one or more detailed areas, is invaded by lesions such as brain tumors, cerebrovascular diseases, brain inflammatory diseases, and trauma. In an embodiment, the language area invasion-related data may be expressed as a probability value regarding whether the language area is invaded. In another embodiment, the language area invasion-related data may be expressed as the language area being invaded when the probability value regarding whether the language area is invaded is greater than or equal to a predetermined value. In another embodiment, the language area invasion-related data may express information about the type of lesion invading the language area, and may express a probability value according to the type of lesion.

The detailed invasion area data according to some embodiments of the present disclosure may be data indicating whether one or more detailed areas constituting the brain language area are invaded. In a specific embodiment, the detailed invasion area data may express the probability that each detailed area constituting a language area is invaded by a lesion. Alternatively, the detailed invasion area data may be a value for expressing the detailed area invaded by the lesion and may be expressed as texts or numbers. In still another embodiment, when the probability that each detailed area constituting the language area is invaded by a lesion is greater than a predetermined standard, the detailed invasion area data may be expressed as each detailed area being invaded. The language area invasion determination according to step S300 is described in detail later with reference to FIG. 6.

When the examiner's language area invasion determination is achieved in step S300, the processor according to some embodiments of the present disclosure may evaluate a speaker's utterance function (S400). For convenience of illustration, step S400 is shown in FIG. 3 as following step S300, but step S300 and step S400 may be performed simultaneously. In some embodiments of the present disclosure, the evaluation of the speaker's utterance function may refer to a step of evaluating a level of the utterance function of the speaker who uttered the test utterance data compared to the normal function. In some embodiments, the evaluation of the speaker's utterance function according to step S400 may be performed by calculating the similarity between reference utterance data and the examiner's test utterance data. In a specific embodiment, the reference utterance data may be utterance data obtained from a person expected to be able to perform a standard utterance function, such as a non-disease patient without a problem with the utterance function or an announcer. The performance of the utterance function evaluation according to step S400 will be described in detail later with reference to FIG. 6.

FIG. 4 is a conceptual diagram showing training utterance data 400, according to some embodiments of the present disclosure. Referring to FIG. 4, utterance data according to some embodiments of the present disclosure may include utterance feature data. When the utterance data is training utterance data 400, the utterance data may further include language area invasion determination data. In some embodiments of the present disclosure, the utterance feature data may include utterance data, speech data, and transcript data. In this case, the language area invasion determination data may include language area invasion-related data and detailed invasion area data. The language area invasion-related data and the detailed invasion area data may include brain imaging-based data.

In some embodiments of the present disclosure, the utterance feature data may be related to characteristics of the speaker's utterance itself, or may be metadata regarding utterance-related characteristics. In particular, the utterance data may be an identifier capable of identifying the utterance data. The speech data may be speech data of an utterance itself or an identifier for the utterance data. The transcript data may be data obtained by transcribing utterance speech data into texts or may be an identifier for such the data.

In some embodiments of the present disclosure, the training utterance data 400 may further include language area invasion-related data or detailed invasion area data. In some embodiments of the present disclosure, the language area invasion-related data or the detailed invasion area data may be a label for training a language area invasion determination model based on supervised learning. Accordingly, the language area invasion determination model according to some embodiments of the present disclosure may output the results of the input utterance data in a form of a vector or tensor. In still another embodiment, the language area invasion determination model may be implemented to combine the results of the output language area invasion-related data and detailed invasion area data and to output only the determination result regarding language area invasion.

The language area invasion-related data or detailed invasion area data according to some embodiments of the present disclosure may include data based on the speaker's brain image. In some embodiments of the present disclosure, the brain image-based data may include the brain image itself and an identifier for the brain image. Furthermore, the brain image-based data may include read data about brain images. In some embodiments of the present disclosure, the brain images may be read results according to conventional MRI, functional MRI (fMRI), DTI tractography, and intraoperative mapping. Referring to FIG. 4, brain image read data according to some embodiments of the present disclosure may express only whether a language area is invaded, but may also express a detailed invasion area. In an embodiment, the fMRI determination result, the DTI tractography determination result, and the intraoperative mapping determination result, which are brain image read data, may express a probability value regarding whether the language area is invaded. Alternatively, in the brain image read data, language area invasion may be expressed as 0 or 1 based on whether the probability value regarding whether a language area is invaded is greater than or equal to a predetermined value. Alternatively, the brain image read data may be expressed as a text or value capable of identifying the detailed area thus invaded. Referring to FIG. 4, output values of brain image read data for one utterance feature data may be different from each other. In the case of utterance data 1 in FIG. 4, all values of the fMRI determination result, the DTI tractography determination result, and the intraoperative mapping determination result are the same as each other. However, in the case of utterance data 2 and utterance data 3, determination result values may be different from each other. In some embodiments of the present disclosure, the language area invasion determination model may learn all different determination result values, or may be learned by using only the determination result values, which match each other by more than half of the values. In detail, in case of utterance data 2, the language area invasion determination model may ignore the invasion determination for area 48, which is the intraoperative mapping determination result, and may perform training as only area 45 being invaded for utterance data 2.

Figure 5:
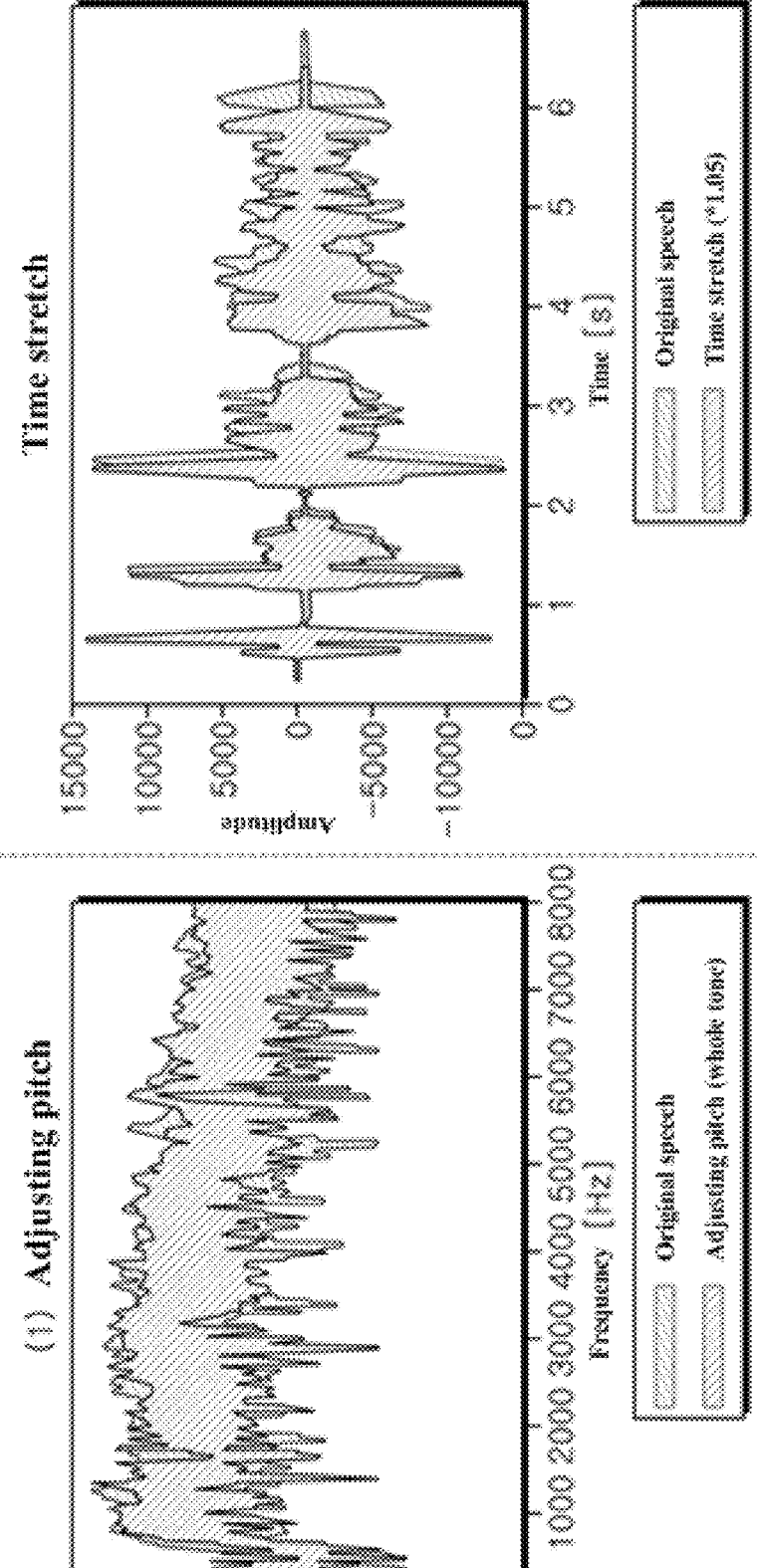
FIG. 5 is a conceptual diagram showing modulation utterance data, according to some embodiments of the present disclosure.

FIG. 5 is a conceptual diagram showing modulation utterance data, according to some embodiments of the present disclosure.

In some embodiments of the present disclosure, training dataset may include one or more training utterance data, and this training utterance data may include not only a speaker's original utterance data, but also modulation utterance data. The modulation utterance data according to some embodiments of the present disclosure may be the result of applying a data augmentation technique to utterance speech data or utterance transcript data. In some embodiments, this modulation utterance data may be modulated to be similar to the original utterance data. Accordingly, the modulation utterance data may be other data having the same label value as the original utterance data. Referring to FIG. 5, the utterance speech data may be modulated by adjusting the pitch of an original speech or performing time stretching on the original speech.

Although not shown in FIG. 5, generation of modulation utterance data may be performed not only on utterance speech data but also on utterance transcript data. In this case, the modulation utterance data may be done in a method of exchanging some words included in the original utterance transcript data with synonyms or changing some preposition included in the original utterance transcript data. The modification of the original utterance transcript data may prevent grammatical errors from occurring while the meaning of the original utterance data is maintained. Alternatively, to construct modulation data more realistically, some of modulation details of the utterance modulation data may be implemented to involve grammatical errors or to include grammatical errors of the original utterance transcript data. Because the number of brain disease patients is sparse compared to non-disease patients, there may be difficulties in securing utterance data for patients with brain disease, and this may affect the degree of training in determining language area invasion model. The issues may be overcome by building utterance data necessary for training the language area invasion model by using various data augmentation techniques. For example, specific text-based patient utterance data may be generated by using an artificial intelligence-based text-to-speech. The training utterance data may include the speaker's original utterance data, the modulation utterance data, and the text-based utterance data.

Figure 6:
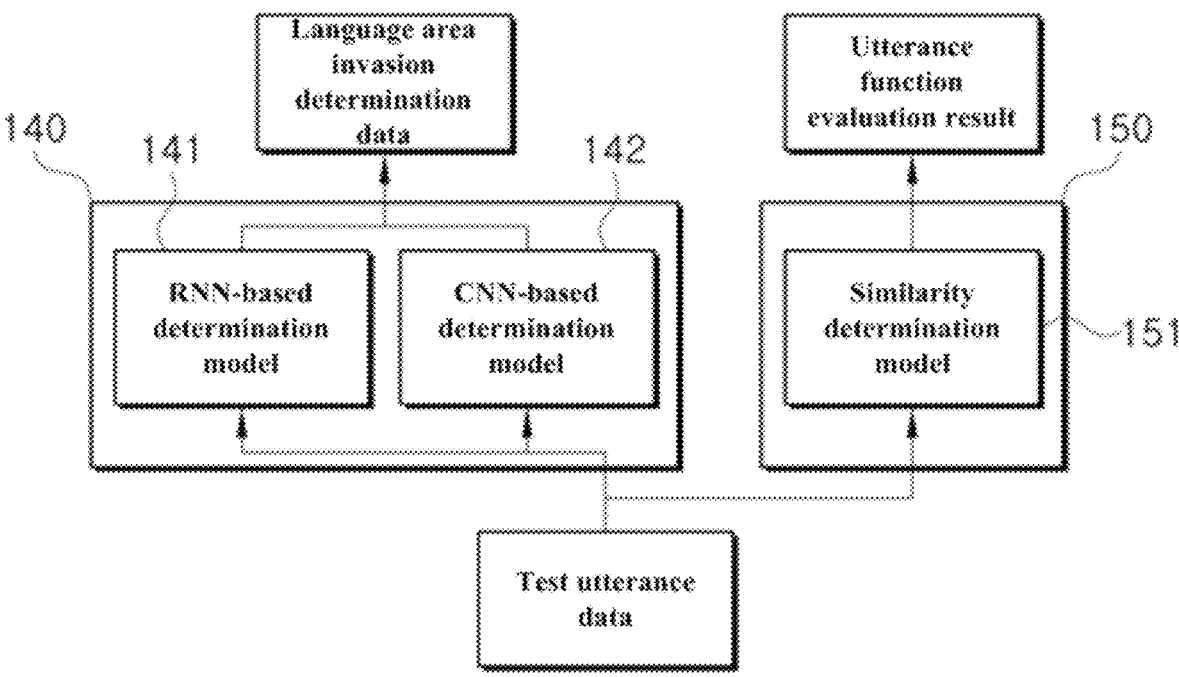
FIG. 6 is a block diagram showing a process of determining language area invasion of a language area invasion determination model and evaluating an utterance function of an utterance function evaluation model, according to some embodiments of the present disclosure.

FIG. 6 is a block diagram showing a process of determining language area invasion of a language area invasion determination model and evaluating an utterance function of an utterance function evaluation model, according to some embodiments of the present disclosure. Referring to FIG. 6, a language area invasion determination apparatus according to some embodiments of the present disclosure may include the language area invasion determination model 140 and the utterance function evaluation model 150. The language area invasion determination model 140 according to some embodiments of the present disclosure may refer to a software or hardware module that receives test utterance data and generates language area invasion determination data. In some embodiments of the present disclosure, a language area invasion determination model may be built by using one or more neural networks. In a specific example, a known neural network model constituting a language area invasion determination model may be used. In detail, recurrent neural networks, convolutional neural networks, transformers, and long short-term memory may be used. As shown in FIG. 6, the language area invasion determination model may include an RNN-based determination model 141 and a CNN-based determination model 142. In some embodiments of the present disclosure, the RNN-based determination model may be a neural network having a structure, in which it is easy to process data with time-series characteristics, such as RNN, GRU, or LSTM. The RNN-based determination model 141 according to some embodiments of the present disclosure may receive utterance speech data or utterance transcript data with time-series characteristics and may generate language area invasion determination data. As described above in FIG. 4, the language area invasion determination data according to some embodiments of the present disclosure may include at least one of language area invasion-related data or detailed invasion area data.

Referring again to FIG. 6, as described above in FIG. 5, when utterance data has an image format, such as an image for a waveform, the CNN-based determination model 142 according to some embodiments of the present disclosure may be a convolution-based neural network model that receives the test utterance data and generates the language area invasion determination data. In particular, the CNN-based determination models such as AlexNet, VGGNet, ResNet, and RegNet may be used.

Although not shown in FIG. 6, the language area invasion determination model 140 according to an embodiment of the present disclosure may further include a sentence reading network that receives the utterance transcript data and generates the language area invasion determination data. In an embodiment, the sentence reading network may be constructed by using an RNN-based neural network or transformer, which is used in natural language processing. In particular, in some embodiments of the present disclosure, on the basis of the fact that the semantic abnormality of the speaker's sentence suggests detailed areas invaded by brain diseases, the sentence reading network may output detailed invasion area data in the language area invasion determination data.

The language area invasion determination model 140 according to some embodiments of the present disclosure may apply an ensemble technique to one or more neural network models thus included. The language area invasion determination model 140 according to some embodiments of the present disclosure may generate final language area invasion determination data by combining the language area invasion determination data output by the RNN-based determination model 141 and the CNN-based determination model 142. In a specific example, the language area invasion determination model 140 may use a value, which is high, from among probability values regarding whether a language area of each model is invaded, or an average value of the probability values as language area invasion-related data. Moreover, when pieces of detailed invasion area data of models match each other, the language area invasion determination model 140 may use the matching value as detailed invasion area data. When they don't match each other, the language area invasion determination model 140 may use all the pieces of detailed invasion area data for models.

The utterance function evaluation model according to some embodiments of the present disclosure may be a model that calculates the similarity between normal utterance data and training utterance data or test utterance data, and evaluates a level of the speaker's utterance function based on the similarity. In some embodiments of the present disclosure, the normal utterance data may refer to utterance data capable of serving as a reference indicator for a given utterance sentence. The normal utterance data may be data for accurately expressing the voice and meaning of the given utterance sentence in the case of a non-disease patient or an announcer. In some embodiments of the present disclosure, the utterance function evaluation model may calculate the similarity in phenotype between the normal utterance data and the training utterance data or the test utterance data. In detail, the phenotype may include a digitized time-series signal of utterance data, a waveform of utterance data, a spectrum of utterance data, a spectrogram of utterance data, or images corresponding to the digital representation.

Meanwhile, the disclosed embodiments may be implemented in a form of a recording medium storing instructions executable by a computer. The instructions may be stored in a form of program codes, and, when executed by a processor, generate a program module to perform operations of the disclosed embodiments. The recording medium may be implemented as a computer-readable recording medium.

The computer-readable recording medium may include all kinds of recording media in which instructions capable of being decoded by a computer are stored. For example, there may be read only memory (ROM), random access memory (RAM), magnetic tape, magnetic disk, flash memory, optical data storage device, and the like.

Disclosed embodiments are described above with reference to the accompanying drawings. One ordinary skilled in the art to which the present disclosure belongs will understand that the present disclosure may be practiced in forms other than the disclosed embodiments without altering the technical ideas or essential features of the present disclosure. The disclosed embodiments are examples and should not be construed as limited thereto.

According to the above-mentioned problem solving means of the present disclosure, whether a brain language area is invaded is determined by using only the speech data of patients with brain diseases.

Effects of the present disclosure are not limited to the effects mentioned above, and other effects not mentioned will be clearly understood by those skilled in the art from the following description.

While the present disclosure has been described with reference to embodiments, it will be apparent to those skilled in the art that various changes and modifications may be made without departing from the spirit and scope of the present disclosure. Therefore, it should be understood that the above embodiments are not limiting, but illustrative.

What is claimed is:

1. A language area invasion determination apparatus comprising:
a memory unit including a language area invasion determination model; and
a processor configured to control an operation of the language area invasion determination model included in the memory unit,
wherein the processor is configured to:
train the language area invasion determination model by using one or more training utterance data; and
output language area invasion determination data of an examiner by using test utterance data and the trained language area invasion determination model, and
wherein the training utterance data and the test utterance data include utterance speech data of a speaker,
wherein the language area invasion determination data comprise language area invasion-related data and detailed invasion area data,
wherein the language area invasion-related data indicate whether a brain language area, which encompasses one or more detailed areas, is invaded by lesions, and the language area invasion-related data are expressed as the brain language area being invaded when a probability value regarding whether the language area is invaded is greater than or equal to a predetermined value, and
wherein the detailed invasion area data indicate whether each area of the one or more detailed areas is invaded, and the detailed invasion area data are expressed as each area of the one or more detailed areas being invaded when a probability value regarding whether each area of the one or more detailed areas is invaded is greater than or equal to the predetermined value.

2. The language area invasion determination apparatus of claim 1, wherein the training utterance data further includes the language area invasion determination data, and
wherein the language area invasion determination data includes at least one of language area invasion-related data or detailed invasion area data.

3. The language area invasion determination apparatus of claim 2, wherein the language area invasion-related data or the detailed invasion area data includes brain image-based data of the speaker.

4. The language area invasion determination apparatus of claim 3, wherein the brain image-based data includes a brain image of the speaker or brain image read data, and
wherein the brain image includes at least one of functional MRI (fMRI), DTI tractography, and intraoperative mapping.

5. The language area invasion determination apparatus of claim 1, wherein the training utterance data includes original utterance data, modulation utterance data, and utterance data generated by using an artificial intelligence-based text-to-speech.

6. The language area invasion determination apparatus of claim 1, wherein the language area invasion determination model is built by using one or more neural networks, and applies an ensemble technique to the one or more neural networks.

7. The language area invasion determination apparatus of claim 6, wherein the applying of the ensemble technique to the one or more neural networks includes:

inputting, by the language area invasion determination model, utterance data into the one or more neural networks, and ensembling language area invasion determination data generated from each of the one or more neural networks, and wherein the one or more neural networks use a recurrent neural network, a convolutional neural network, a transformer, and a long short-term memory.

8. The language area invasion determination apparatus of claim 7, wherein the utterance data further includes utterance transcript data.

9. The language area invasion determination apparatus of claim 8, wherein the language area invasion determination model further includes a sentence reading network that receives the utterance transcript data and generates language area invasion determination data.

10. The language area invasion determination apparatus of claim 9, wherein the sentence reading network outputs detailed invasion area data.

11. The language area invasion determination apparatus of claim 1, wherein the processor is configured to:

train an utterance function evaluation model of the speaker by using the training utterance data, and wherein the utterance function evaluation model calculates a similarity between normal utterance data and the training utterance data or the test utterance data.

12. The language area invasion determination apparatus of claim 11, wherein the calculating of the similarity between the normal utterance data and the training utterance data or the test utterance data includes:

calculating a similarity between a waveform of the normal utterance data and a waveform of the training utterance data or a waveform of the test utterance data.

13. A method performed by a language area invasion determination apparatus, method comprising:

training a language area invasion determination model by using one or more training utterance data; and outputting language area invasion determination data of an examiner by using test utterance data and the trained language area invasion determination model, and wherein the training utterance data and the test utterance data include utterance speech data of a speaker, wherein the language area invasion determination data comprise language area invasion-related data and detailed invasion area data, wherein the language area invasion-related data indicate whether a brain language area, which encompasses one or more detailed areas, is invaded by lesions, and the language area invasion-related data are expressed as the brain language area being invaded when a probability value regarding whether the language area is invaded is greater than or equal to a predetermined value, and wherein the detailed invasion area data indicate whether each area of the one or more detailed areas is invaded, and the detailed invasion area data are expressed as each area of the one or more detailed areas being invaded when a probability value regarding whether each area of the one or more detailed areas is invaded is greater than or equal to the predetermined value.

14. The method of claim 13, wherein the training utterance data further includes the language area invasion determination data, and wherein the language area invasion determination data includes at least one of language area invasion-related data or detailed invasion area data.

15. The method of claim 14, wherein the language area invasion-related data or the detailed invasion area data includes brain image-based data of the speaker.

16. The method of claim 15, wherein the brain image-based data includes a brain image of the speaker or brain image read data, and wherein the brain image includes at least one of fMRI, DTI tractography, and intraoperative mapping.

17. The method of claim 13, wherein the training utterance data includes original utterance data, modulation utterance data, and utterance data generated by using an artificial intelligence-based text-to-speech.

18. The method of claim 13, wherein the language area invasion determination model is built by using one or more neural networks, and applies an ensemble technique to the one or more neural networks.

19. The method of claim 18, wherein the applying of the ensemble technique to the one or more neural networks includes:

inputting, by the language area invasion determination model, utterance data into the one or more neural networks, and ensembling language area invasion determination data generated from each of the one or more neural networks, and wherein the one or more neural networks use a recurrent neural network, a convolutional neural network, a transformer, and a long short-term memory.

20. The method of claim 19, wherein the utterance data further includes utterance transcript data, wherein the language area invasion determination model further includes a sentence reading network that receives the utterance transcript data and generates language area invasion determination data, and wherein the sentence reading network outputs detailed invasion area data.

\*    \*    \*    \*    \*